(12) United States Patent
Scandurra et al.

(10) Patent No.: US 9,987,153 B2
(45) Date of Patent: Jun. 5, 2018

(54) VASCULAR ELASTANCE

(75) Inventors: John Scandurra, St. Paul, MN (US);
Karl Vollmers, Minneapolis, MN (US);
Christopher Scorzelli, St. Paul, MN (US); Eric F. Little, Shakopee, MN (US)

(73) Assignee: The Regents Of The University of Minnesota, Minneapolis, MN (US)

( * ) Notice: Subject to any disclaimer, the term of this patent is extended or adjusted under 35 U.S.C. 154(b) by 0 days. days.

(21) Appl. No.: 13/701,721

(22) PCT Filed: May 31, 2011

(86) PCT No.: PCT/US2011/038558
§ 371 (c)(1),
(2), (4) Date: Dec. 3, 2012

(87) PCT Pub. No.: WO2011/156176
PCT Pub. Date: Dec. 15, 2011

(65) Prior Publication Data
US 2013/0079871 A1 Mar. 28, 2013

Related U.S. Application Data

(60) Provisional application No. 61/352,774, filed on Jun. 8, 2010.

(51) Int. Cl.
*A61F 2/82* (2013.01)
*A61F 2/06* (2013.01)
(Continued)

(52) U.S. Cl.
CPC .......... *A61F 2/82* (2013.01); *A61B 17/12036* (2013.01); *A61B 17/12109* (2013.01);
(Continued)

(58) Field of Classification Search
CPC .............. A61F 2/958; A61F 2002/9583; A61F 2002/9586; A61F 2/82; A61F 2/06;
(Continued)

(56) References Cited

U.S. PATENT DOCUMENTS 3,275,001 A 9/1966 Rosecrans
3,634,924 A 1/1972 Blake et al.
(Continued)

FOREIGN PATENT DOCUMENTS

CN 102657910.1 9/2012
DE 195 08 129 C2 2/1997
(Continued)

OTHER PUBLICATIONS

International Search Report from the International Patent Application Serial No. PCT/US11/38558, U.S. Receiving Office, dated Sep. 8, 2011, 1 page.
(Continued)

*Primary Examiner* — Christopher D Prone
*Assistant Examiner* — Rokhaya Diop
(74) *Attorney, Agent, or Firm* — Foley & Lardner LLP; Christopher C. Bolten; Nicola A. Pisano

(57) ABSTRACT

A device includes a balloon and an interface. The balloon has an outer surface and a central lumen aligned on a longitudinal axis. The balloon is configured to receive a compressible fluid. The interface is coupled to the outer surface and has an external surface configured to bond with a tissue.

9 Claims, 9 Drawing Sheets

(51) Int. Cl.
*A61F 2/848* (2013.01)
*A61B 17/12* (2006.01)

(52) U.S. Cl.
CPC .......... *A61B 17/12136* (2013.01); *A61F 2/06* (2013.01); *A61F 2/848* (2013.01); *A61F 2250/0003* (2013.01); *A61F 2250/0013* (2013.01)

(58) Field of Classification Search
CPC .............. A61F 2/848; A61F 2250/0013; A61F 2250/0003; A61M 29/00; A61M 29/02; A61M 25/104; A61M 2025/1047; A61M 2025/1075; A62B 17/12022; A61B 17/12136; A61B 17/12036; A61B 17/12109
USPC .................. 623/1.12, 1.13, 1.14, 1.25, 23.67; 606/191, 192, 194
See application file for complete search history.

(56) References Cited

U.S. PATENT DOCUMENTS

| | | | |
|---|---|---|---|
| 3,818,903 | A | 6/1974 | Bleecker |
| 4,422,447 | A | 12/1983 | Schiff |
| 4,793,351 | A | 12/1988 | Landman et al. |
| 4,902,273 | A | 2/1990 | Choy et al. |
| 4,938,766 | A | 7/1990 | Jarvik |
| 4,955,905 | A | 9/1990 | Reed |
| 5,002,531 | A | 3/1991 | Bonzel |
| 5,112,303 | A | 5/1992 | Pudenz et al. |
| 5,222,980 | A | 6/1993 | Gealow |
| 5,409,444 | A | 4/1995 | Kensey et al. |
| 5,713,867 | A | 2/1998 | Morris |
| 5,769,821 | A | 6/1998 | Abrahamson et al. |
| 5,795,325 | A | 8/1998 | Valley et al. |
| 5,814,016 | A | 9/1998 | Valley et al. |
| 5,820,542 | A | 10/1998 | Dobak et al. |
| 5,833,655 | A | 11/1998 | Freed et al. |
| 6,017,324 | A | 1/2000 | Tu et al. |
| 6,030,336 | A | 2/2000 | Franchi |
| 6,053,891 | A | 4/2000 | Decampli |
| 6,136,025 | A | 10/2000 | Barbut et al. |
| 6,210,318 | B1 | 4/2001 | Lederman |
| 6,261,304 | B1 | 7/2001 | Hall et al. |
| 6,461,367 | B1 | 10/2002 | Kirsch et al. |
| 6,558,349 | B1 | 5/2003 | Kirkman |
| 6,559,349 | B1 | 5/2003 | Slaugh et al. |
| 6,576,007 | B2 | 6/2003 | Dehdashtian et al. |
| 6,579,224 | B1 | 6/2003 | Burton et al. |
| 6,682,473 | B1 | 1/2004 | Matsuura et al. |
| 7,044,967 | B1 | 5/2006 | Solem et al. |
| 7,074,178 | B2 | 7/2006 | Connors et al. |
| 7,468,050 | B1 | 12/2008 | Kantrowitz |
| 7,540,876 | B2 | 6/2009 | Connors et al. |
| 7,766,814 | B2 | 8/2010 | Walsh |
| 7,811,249 | B2 | 10/2010 | Saab |
| 7,928,367 | B2 | 4/2011 | Hirota et al. |
| 8,092,521 | B2 | 1/2012 | Figulla et al. |
| 8,116,883 | B2 | 2/2012 | Williams et al. |
| 8,206,378 | B1 | 6/2012 | Kalpin et al. |
| 8,585,572 | B2 | 11/2013 | Mehmanesh |
| 8,747,386 | B2 | 6/2014 | Rykhus et al. |
| 8,876,850 | B1 | 11/2014 | Vollmers et al. |
| 9,017,359 | B2 | 4/2015 | Scandurra et al. |
| 9,039,725 | B1 | 5/2015 | Vollmers et al. |
| 9,107,992 | B2 | 8/2015 | Kushwaha et al. |
| 2001/0023332 | A1 | 9/2001 | Hahnen |
| 2003/0055465 | A1 | 3/2003 | Ben-Haim et al. |
| 2003/0208259 | A1* | 11/2003 | Penhasi ........................ 623/1.15 |
| 2004/0093007 | A1 | 5/2004 | Sussman et al. |
| 2004/0106971 | A1* | 6/2004 | Schwartz ............ A61B 17/0057 623/1.1 |
| 2004/0111006 | A1 | 6/2004 | Alferness et al. |
| 2004/0143319 | A1 | 7/2004 | Schwartz et al. |
| 2004/0210304 | A1 | 10/2004 | Seguin et al. |
| 2005/0015107 | A1 | 1/2005 | O'Brien |
| 2005/0059965 | A1 | 3/2005 | Eberl et al. |
| 2005/0070938 | A1 | 3/2005 | Copa et al. |
| 2005/0267596 | A1 | 12/2005 | Chen et al. |
| 2006/0085028 | A1 | 4/2006 | Boock |
| 2006/0106450 | A1 | 5/2006 | Ben Muvhar |
| 2006/0129083 | A1 | 6/2006 | Brenneman et al. |
| 2006/0135962 | A1 | 6/2006 | Kick et al. |
| 2006/0155310 | A1 | 7/2006 | Binmoeller |
| 2006/0241745 | A1 | 10/2006 | Solem |
| 2006/0253095 | A1 | 11/2006 | Stull |
| 2007/0142819 | A1 | 6/2007 | El-Nounou et al. |
| 2007/0156013 | A1 | 7/2007 | Birk |
| 2007/0156167 | A1* | 7/2007 | Connors et al. .............. 606/194 |
| 2008/0114338 | A1 | 5/2008 | Kumar |
| 2008/0132750 | A1 | 6/2008 | Miller |
| 2008/0194905 | A1* | 8/2008 | Walsh ................. A61F 2/06 600/17 |
| 2008/0195174 | A1 | 8/2008 | Walker et al. |
| 2008/0243093 | A1 | 10/2008 | Kalpin et al. |
| 2008/0312679 | A1 | 12/2008 | Hardert et al. |
| 2009/0143837 | A1 | 6/2009 | Rossing et al. |
| 2009/0222083 | A1 | 9/2009 | Nguyen et al. |
| 2009/0240277 | A1 | 9/2009 | Conners et al. |
| 2009/0294031 | A1 | 12/2009 | Pepper et al. |
| 2010/0042070 | A1 | 2/2010 | Gill et al. |
| 2010/0099945 | A1 | 4/2010 | Birk et al. |
| 2010/0185049 | A1 | 7/2010 | Birk et al. |
| 2010/0197994 | A1 | 8/2010 | Mehmanesh |
| 2010/0274221 | A1 | 10/2010 | Sigg et al. |
| 2010/0324472 | A1 | 12/2010 | Wulfman |
| 2010/0331767 | A1 | 12/2010 | Frankowski et al. |
| 2011/0124951 | A1 | 5/2011 | Walsh |
| 2011/0137210 | A1 | 6/2011 | Johnson |
| 2011/0137428 | A1 | 6/2011 | Terliuc |
| 2012/0053514 | A1 | 3/2012 | Robinson et al. |
| 2012/0083646 | A1 | 4/2012 | Benson |
| 2012/0172654 | A1 | 7/2012 | Bates |
| 2013/0079871 | A1 | 3/2013 | Scandurra et al. |
| 2013/0165964 | A1 | 6/2013 | Vollmers et al. |
| 2013/0245665 | A1 | 9/2013 | Scandurra et al. |
| 2014/0214149 | A1 | 7/2014 | Kuraguntla et al. |
| 2014/0228878 | A1 | 8/2014 | Scandurra et al. |
| 2015/0196303 | A1 | 7/2015 | Seguin |
| 2015/0216531 | A1 | 8/2015 | Seguin |
| 2015/0282859 | A1 | 10/2015 | Bencini et al. |

FOREIGN PATENT DOCUMENTS

| | | | |
|---|---|---|---|
| DE | 10 2005 060 197 | | 6/2007 |
| EP | 0 366 814 A1 | | 5/1990 |
| EP | 0 959 912 B1 | | 12/1999 |
| EP | 2 016 961 B1 | | 2/2010 |
| FR | 3016279 A1 | | 1/2014 |
| FR | 3017044 A1 | | 1/2014 |
| JP | 2005-538807 | | 12/2005 |
| JP | 2007-526039 | | 9/2007 |
| JP | 2009-502247 | | 1/2009 |
| JP | 2009-509650 | | 3/2009 |
| WO | WO 9004430 A1 * | 5/1990 | ............ A61M 25/10 |
| WO | WO-90/06086 A1 | 6/1990 | |
| WO | WO-93/17731 A1 | 9/1993 | |
| WO | WO-1995/010317 A1 | 4/1995 | |
| WO | WO-95/32018 A1 | 11/1995 | |
| WO | WO-96/00095 A1 | 1/1996 | |
| WO | WO-96/12518 A1 | 5/1996 | |
| WO | WO-96/34647 A1 | 11/1996 | |
| WO | WO-98/50100 A1 | 11/1998 | |
| WO | WO 1999-004833 | 2/1999 | |
| WO | WO-00/66030 A1 | 11/2000 | |
| WO | WO-2002/036048 A1 | 5/2002 | |
| WO | WO-2004/026112 A2 | 4/2003 | |
| WO | WO-2004/026112 A2 | 4/2004 | |
| WO | WO-2005/084730 A1 | 9/2005 | |
| WO | WO-2006/020942 A1 | 2/2006 | |
| WO | WO 2006-067473 | 6/2006 | |
| WO | WO-2007/014028 A1 | 2/2007 | |
| WO | WO-2007/038476 A2 | 4/2007 | |

(56) References Cited

FOREIGN PATENT DOCUMENTS

| | | |
|---|---|---|
| WO | WO-2007/059594 A1 | 5/2007 |
| WO | WO-2008/154145 A1 | 12/2008 |
| WO | WO-2010/022173 A1 | 2/2010 |
| WO | WO-2013/148697 A1 | 10/2013 |
| WO | WO-2013/185138 A1 | 12/2013 |
| WO | WO-2004/080338 A2 | 9/2014 |
| WO | WO-2015/107434 A1 | 7/2015 |
| WO | WO-2015/114471 A1 | 8/2015 |

OTHER PUBLICATIONS

International Search Report and Written Opinion dated Dec. 22, 2015 in Int'l PCT Patent Application Serial No. PCT/US2015/036201.
Second Written Opinion dated Jul. 7, 2016 in Int'l PCT Patent Application Serial No. PCT/US2015/036201.
Borlaug, et al., Ventricular-Vascular Interaction in Heart Failure. Heart Failure Clinics, 4(1):23-36 (2008).
Elzinga, et al., Pressure and flow generated by the left ventricle against different impedances. Circulation Research, 32(2):178-186 (1973).
Elzinga, et al., Left and right ventricular pump function and consequences of having two pumps in one heart. Circ. Res., 46:564-574 (1980).
Grant, et al., Clinical significance of pulmonary arterial input impedance. European Respiratory Journal, 9(11):2196-2199 (1996).
Harnek, et al. Transcatheter implantation of the MONARC coronary sinus device for mitral regurgitation: 1-year results from the EVOLUTION phase I study (Clinical Evaluation of the Edwards Lifesciences Percutaneous Mitral Annuloplasty System for the Treatment of Mitral Regurgitation). JACC: Cardiovascular Interventions, 4(1):115-122 (2011).
Lammers, et al., Mechanics and function of the pulmonary vasculature: implications for pulmonary vascular disease and right ventricular function. Comprehensive Physiology, 2:295-319 (2012).
Lankhaar, et al., Pulmonary vascular resistance and compliance stay inversely related during treatment of pulmonary hypertension. European Heart Journal, 29:1688-1695 (2008).
Mahapatra, et al., Relationship of Pulmonary Arterial Capacitance and Mortality in Idiopathic Pulmonary Arterial Hypertension, Journal of the American College of Cardiology, 47(4):799-803 (2006).
Naeije, et al., Right ventricular function in pulmonary hypertension: physiological concepts. European Heart Journal Supplements 9, Suppl. H, H5-H9 (2007).
Pellegrini, et al., Prognostic Relevance of Pulmonary Arterial Compliance in Patients With Chronic Heart Failure, Chest, Original Research, Pulmonary Vascular Disease, 145(5):1064-1070 (2014).
Procyrion. "A tool for the Cardiologist", published Jul. 3, 2013. http://web.archive.org/web/20130703020540/http://www.procyrion.com/technology.
Reuben, Stuart R., Compliance of the Human Pulmonary Arterial System in Disease, Circulation Research, 29(1):40-50 (1971).
Saouti, et al., The arterial load in pulmonary hypertension, European Respiratory Review, 19(117):197-203 (2010).
Souza, Rogerio, Assessment of compliance in pulmonary arterial hypertension, European Heart Journal, 29:1603-1604 (2008).
Sunagawa, et al., Left ventricular interaction with arterial load studied in isolated canine ventricle, American Journal of Physiology—Heart and Circulatory Physiology, 245(5):H773-H780 (1983).
Wang, et al., Pulmonary vascular wall stiffness: an important contributor to the increased right ventricular afterload with pulmonary hypertension. Pulmonary Circulation, 1(2):212-223 (2011).

* cited by examiner

US 9,987,153 B2

VASCULAR ELASTANCE

BACKGROUND OF THE INVENTION

Pulmonary Hypertension (PH) is a condition characterized by elevated blood pressure in the pulmonary circulation. It can be caused by multiple diseases and if not controlled, leads to right heart failure and death. Depending on the form of the disease, afflicted individuals can have poor quality of life and a very poor prognosis. According to one authority, median survival time for untreated idiopathic pulmonary arterial hypertension in 2002 was 2.8 years. PH can be defined as a mean blood pressure in the pulmonary artery greater than 25 mmHg at rest.

SUMMARY

A healthy artery is an elastic vascular structure that can deform when acted on by mechanical forces. With some diseases, such as arteriosclerosis and hypertension, an artery becomes less compliant than normal. This reduction in compliance results in a relatively high pulsatile pressure in the artery for a given stroke volume. A reduction in arterial compliance increases the hydraulic loading on the heart and increases the amount of energy lost in the pulsatile components. In light of the pulsatile component loading on the right heart, a decrease in arterial compliance can be problematic.

An example of the present subject matter is configured for treating hypertension of the systemic or pulmonary circulations. In hypertension, the relatively low compliance of the arteries can contribute to high peak arterial pressures. The high peak arterial pressure, in turn, causes high peak ventricular wall stress and energy expenditure. Over time, this increases cardiac burden can lead to heart failure, and ultimately, death.

An example of the present subject matter is configured to reduce the pulsatile stiffness component of arterial elastance and as a consequence, improve systemic arterial elastance with the effect of minimizing the afterload on the right heart.

An example of the present subject matter is configured to reduce the pulsatile arterial elastance. In one example, a compressible device is implanted within the blood vessel. The device has a volume (sometimes referred to as a compressible volume) that changes when subjected to pressure within the vessel. For instance, a pressure change within the vessel can cause the device to compress from a first volume to a second volume and thereby provide a reduction in vessel elastance.

In one example, a device includes both a rigid structure and a compressible volume that is configured to encircle an artery. The compressible volume portion can compress during vessel distension. As such, the device functions as a spring. In one example, the device is coupled to a wall of the vessel and is located external to the vessel or partially external to the vessel. In one example, the device is configured for placement within the muscular vessel wall.

In one example, an energy storage device is coupled to a vessel. The device is configured to absorb energy from the system at a first time and return energy to the system during a second time. The energy storage device, in one example, includes a fluidic accumulator having a dynamic element. The dynamic element can include an elastic membrane or a piston. Examples of the present subject matter are suitable for treatment related to heart failure, general hypertension, or pulmonary hypertension.

These and other examples and aspects of the present devices and methods are set forth in the following Detailed Description. This Summary is intended to provide an overview of the subject matter of the present patent document. It is not intended to provide an exclusive or exhaustive explanation of the present invention. The Detailed Description is included to provide further information about the subject matter of the present patent document.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION OF THE INVENTION

Figure 2:
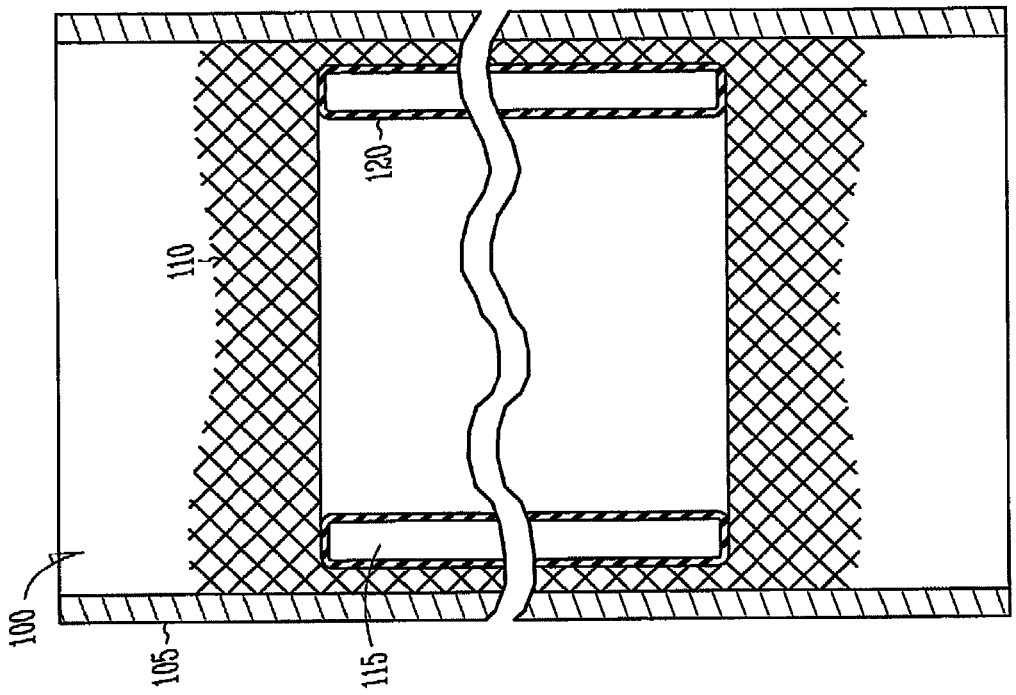
FIG. 2 illustrates a sagittal view of a device according to one example.

In pulmonary hypertension, the structure and function of both the pulmonary artery and right ventricle are altered. Right ventricular performance is influenced by arterial load and arterial properties are, in turn, influenced by right ventricular performance. This interaction, called arterial-ventricular coupling, plays a role in determining cardiovascular performance and cardiac energetics.

Elastance can be expressed as a change in pressure for a given change in volume, $E=\Delta P/\Delta V$. For the pulmonary artery, the Effective Arterial Elastance, $E_{PA}$, represents the total arterial load imposed on the right ventricle (afterload). It is proportional to the sum of the steady state resistive component (Cardiac Output Pulmonary Vascular resistance)+the pulsatile, stiffness component (End Systolic Pressure-Mean Arterial Pressure/Stroke Volume)+the load generated by reflected waves.

Afterload is caused by the dynamic interplay between steady state resistance, dynamic stiffness and wave reflections. In Pulmonary Arterial Hypertension, both the steady state and the pulsatile components of afterload are increased. In addition, the altered Pulmonary Arterial stiffness and right ventricular timing cause the reflected waves to significantly contribute to ventricular afterload, whereas in a normal individual reflected waves have a much smaller effect.

Compliance is a measure of the ability of an elastic body to accommodate deformation. When considering a closed volume, compliance is defined as the ratio of the change of internal volume to the change in internal pressure due to an externally applied force. Mathematically, compliance can be expressed as $C=\Delta V/\Delta P$ and is the multiplicative inverse (or reciprocal) of elastance.

The right and left ventricles of the heart pump blood into the pulmonary artery and aorta respectively. As the heart undergoes systole and diastole, pulsatile flow is generated such that localized periodic pressure rises and falls about the mean arterial pressure. A time response of blood pressure at a particular location along the artery exhibits a periodic variation of pressure levels about the mean that is correlated with systole and diastole.

In addition to the pulmonary artery, examples of the present subject matter can be used to increase the compliance of other fluid-carrying organs. As used herein, an organ includes tissue having a particular function. An organ can be a component of an anatomical system such as vessel in a circulatory system. One example of the present subject matter is configured to increase the compliance of a vessel (such as an artery, a capillary, or a vein) or other hollow organ. A hollow organ can include a visceral organ having a hollow tube or pouch (such as the stomach or intestine) or that includes a cavity (such as the heart or urinary bladder). For instance, one example is configured for placement in a component of the urinary system and may be suitable for treatment of incontinence.

An example of the present subject matter includes an energy absorbing device configured to respond to fluidic pressure changes within an organ. As such, the device provides a smoothing function as to changes in the fluid pressure. For example, the maximum pressure is reduced and the minimum pressure is raised. The change in pressure dynamics can also include a shift in the mean pressure level within the organ.

Consider one example in which the present subject matter is configured for placement in an artery of a vascular system. In such an example, an energy storage device is coupled to the artery to increase tissue compliance. The energy storage device can include a compliant member located within the artery, a compliant member coupled to the artery by a fluidic channel, or a compliant member wholly or fully embedded in a wall of the artery. In one example, the energy storage device can include a fluidic accumulator. In another example, the energy storage device can include a compliant member having a flexible membrane that surrounds a compliant volume.

A flexible membrane can include a structure whose stiffness can be changed. The stiffness can be changed by changing pressure within the compliant volume by various means including direct variation of internal pressures such as injection of gas through a catheter or needle, transfer of material from a small volume of relatively high pressure to a larger volume of relatively lower pressure, conversion of material from solid to gas, conversion of material from liquid to gas or the addition of compliant materials such as gas, foam, or hydro-gel.

The stiffness of the flexible membrane can also be changed by selection of the membrane material or selection of the membrane thickness. In addition, the stiffness can be changed by selection of the membrane geometry. In one example, the stiffness is remotely adjustable using an external energy source such as ultrasound, electromagnetic waves, or magnetic field variations such as an electrically induced vaporizer.

A compliant volume is a structure substantially bounded on all sides by surfaces that can include, among others, a flexible membrane or a piston. The compliance of the compliant volume can be adjusted by changing the pressure within the compliant volume by various means including direct variation of internal pressures or the addition of compliant materials such as gas, foam, or hydro-gel. In addition, material selection and thickness can be used to tailor a particular compliant volume. Adjustments can also be made in the geometry of the compliant volume or by using an induced vaporizer or gas generator.

Differential pressure is the instantaneous variation of pressure between that experienced in the bodily lumen and that experienced in the compliant volume defined by the compliant body. A positive differential pressure indicates lumen pressure exceeds compliant volume pressure. A negative differential pressure indicates compliant volume pressure exceeds lumen pressure.

An example of the present subject matter can be held in place, or anchored, by various structures. The present subject matter is anchored to reduce the risk presented by an embolized structure. For example, a device can be anchored by a suture, a stent, a friction fit, expansion to fill a hollow or vascular space, a hook mechanism, vascular endothelial in-growth, a barb mechanism, a rivet, compression exerted by adjacent tissue, or a magnet.

An example of the present subject matter can be delivered to the installation site by various procedures, including a surgical procedure or a percutaneous procedure. For example, general surgery, percutaneous transcatheter surgery, thorascopically, and intra or extra vascular placement can be used. A minimally invasive surgical procedure can be used to install a device. A percutaneous installation procedure can include using a needle, an introducer guide wire, an introducer sheath, and a catheter. The catheter can also be used to inflate or pressurize the device after installation. Such methods and tools can also be used for device removal or to reposition a device.

In one example, the device is fabricated of a material that is biocompatible. In addition, one example includes a biologically absorbable material. Other materials can also be used. For example, a material that assists in the growth of endothelial cells on a surface can be used for various components. In one example, a component is fabricated of a material having a smooth, low friction surface that facilitates implantation or removal.

Device fabrication can include manufacturing a balloon. In addition, molded or formed materials, such as sheet goods, can be used in the fabrication of such a device. A fatigue resistant polymer having sufficient flexibility can be used for a membrane. In one example, a membrane is fabricated using a sputter-coating (diffusion layer) to limit gas pass-through.

Figure 1:
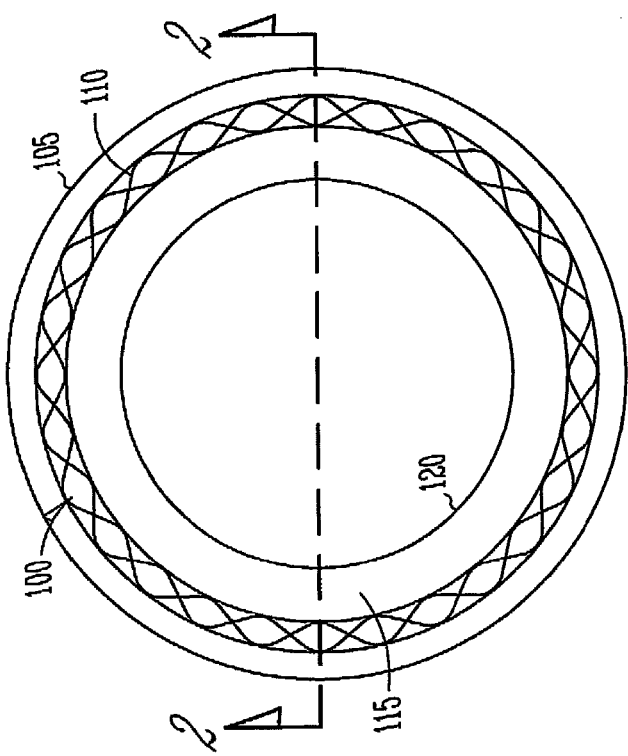
FIG. 1 illustrates a transverse view of a device according to one example.

FIGS. 1 and 2 illustrate transverse and sagittal views, respectively, of device 100 according to one example. In the example illustrated, device 100 includes interface 110 and compliant body 115. Interface 110 includes a stent-like anchoring device and is configured, in this example, for placement within a blood vessel, such as artery 105. Channel 120 is a lumen aligned with artery 105 and carries blood.

Interface 110 can include a metal or non-metal mesh selected to promote bonding with the endothelium layer. The endothelium is a thin layer of cells that line the interior of blood vessels, thus forming an interface between circulating blood lumen and the vessel wall.

In one example, interface 110 forms a fluid-tight joint with the inner surface of the walls of artery 105. In one example, interface 110 is loosely fitted within artery 105 and blood, or other fluid, is allowed to pass between compliant body 115 and the inner surface of the walls of artery 105. Device 100 can be retained in artery 105 by an interference fit with the vessel wall.

Compliant body 115 presents a compliant volume. The undeformed shape of the compliant volume is defined by a resilient or flexible membrane of compliant body 115. Compliant body 115 can readily deform to assume a variety of shapes including, but not limited to, cylindrical, ellipsoidal, polygonal cross-sections with mitered, concave, or convex features along the length of the central compliant volume. In one example, compliant body 115 includes a toroidal cylindrical shape of a length and a diameter corresponding to the compliant volume.

Device 100 is held in fixed alignment relative to the vasculature using an anchor structure. In the example shown, the outer surface of compliant body 115 is fastened to interface 110. Interface 110 includes a stent-like component which expands on deployment to intimately contact the wall of artery 105 to reduce embolization of the device 100. In one example, device 100 is located within the lumen of artery 105 and interface 110 allows device 100 to be suspended within the lumen.

In operation, the device 100 is located within the vasculature and is exposed to pulsatile pressure loads. Under positive differential pressure, blood flowing in artery 105 exerts a force against device 100 and deforms the compliant body 115 such that an equivalent volume of blood occupies the space of the compliant body 115. Under negative differential pressure, the compliant body 115 returns to the original, undeformed position.

Figure 3:
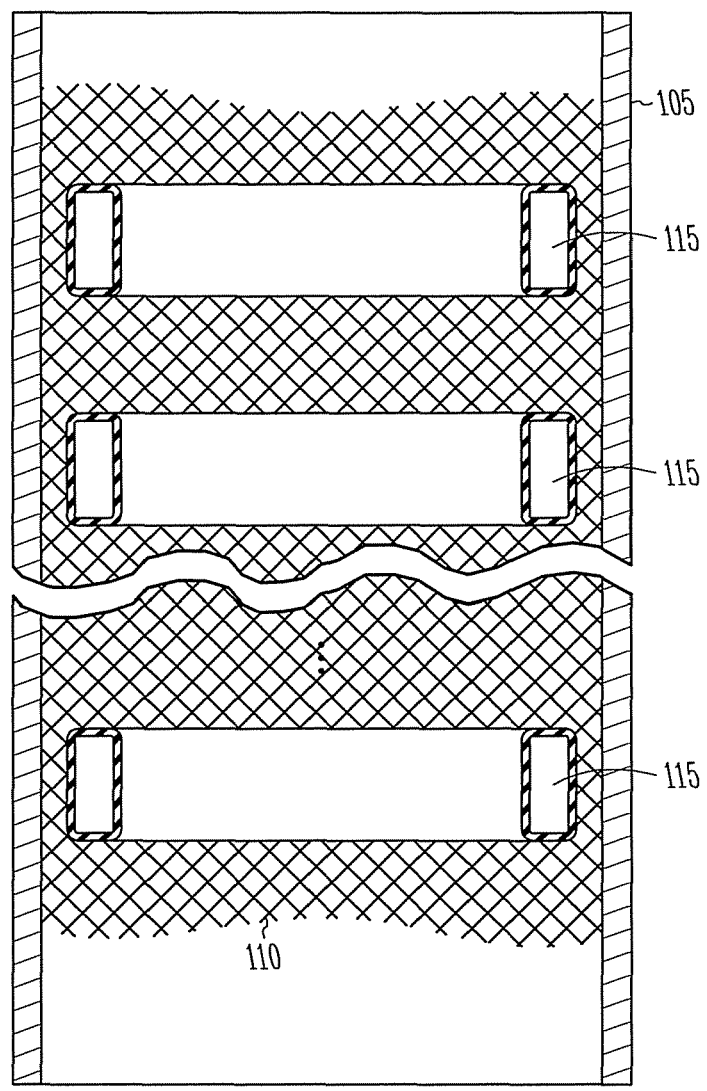
FIG. 3 illustrates a sagittal view of a device having multiple segments according to one example.

FIG. 3 illustrates a sagittal cross sectional view of an example having a plurality of annular compliant bodies 115 coupled to a common interface 110 disposed in artery 105. In this example, each compliant body 115 operates independently of any other compliant body 115.

The number of individual compliant bodies 115 is not limited and is selectable according to the compliancy requirements of a particular application.

Figure 5:
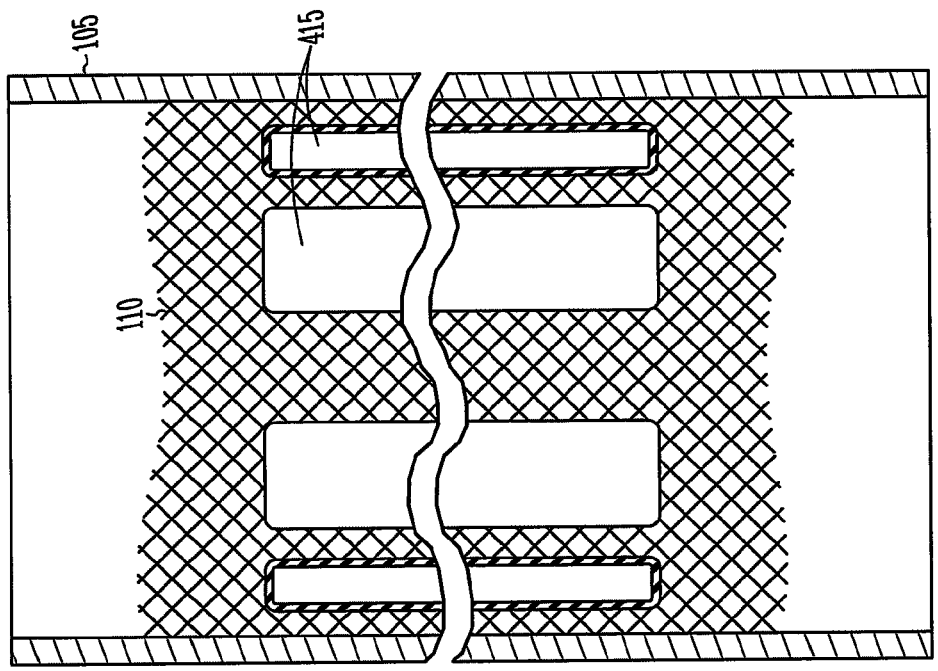
FIG. 5 illustrates a sagittal view of a device having multiple segments according to one example.
Figure 4:
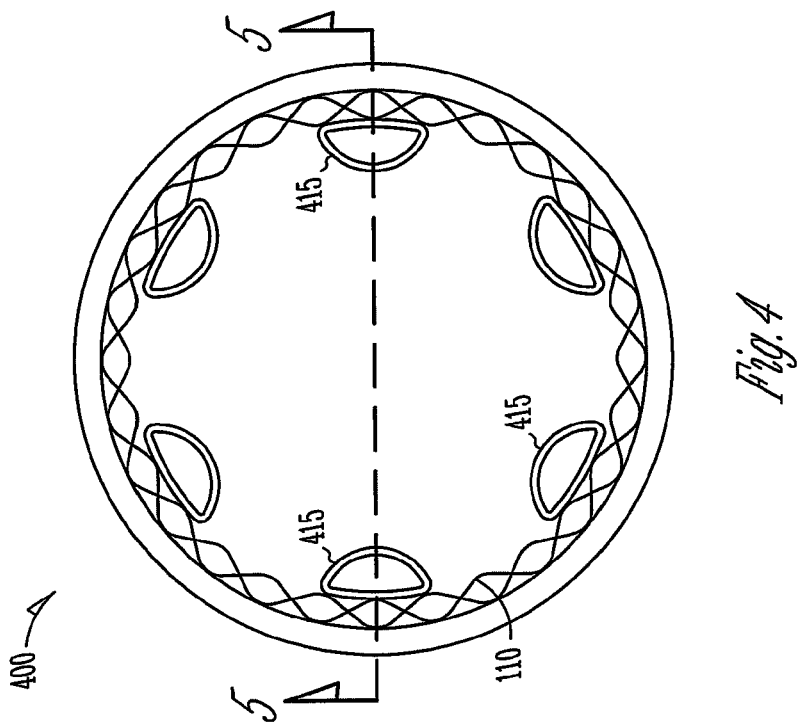
FIG. 4 illustrates a transverse view of a device having multiple segments according to one example.

FIGS. 4 and 5 illustrate views of an example having a plurality of longitudinal compliant bodies 415 and interface 110 disposed in artery 105. The compliant bodies 415 in this example are distributed about the interior of the artery and each has a rounded linear profile. The particular profile is selected to provide a variable volume region that is distributed in a manner to maintain uniform blood flow within a large portion of the lumen. A variety of profiles are contemplated, including cylindrical, ellipsoidal, polygonal cross-sections with mitered, concave, or convex features along the length of each individual compliant body 415.

The examples shown includes a common interface 110, however, a plurality of individual segments of interface 110 can also be used.

Figure 6:
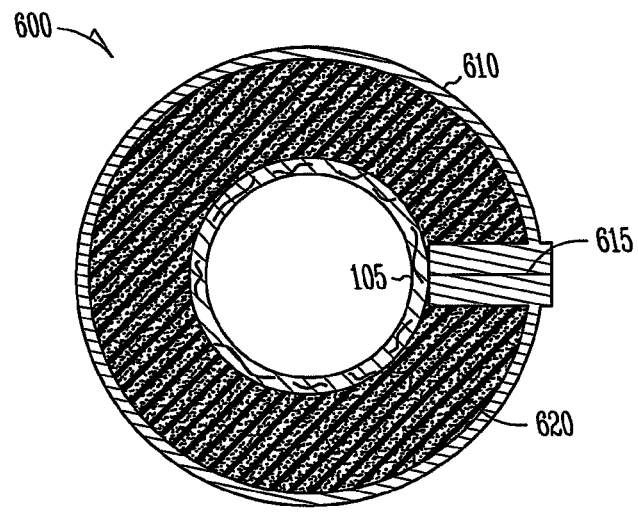
FIG. 6 illustrates a lateral cross sectional view of a device having an extra-vascular compliant member according to one example.

FIG. 6 illustrates a lateral cross section view of device 600 according to one example. Device 600 includes compliant body 620 configured to surround the periphery of artery 105. Compliant body 620 can have a shape defined by a flexible membrane (or balloon) and can have a variety of shapes, including cylindrical, ellipsoidal, polygonal cross-sections with mitered, concave, or convex features along the length of the compliant body 620. In the example shown, compliant body 620 includes a flexible membrane having a toroidal shape with a circular cross-sectional area and a length selected to encompass a volume sufficient to provide a therapeutic effect. Compliant body 620 can include a sheet of material suitable for wrapping around artery 105. In the example shown, compliant body 620 is wrapped and joined in the area near joint 615.

Shell 610 surrounds the outer surface of compliant body 620. In the example illustrated, shell 610 is wrapped around artery 105 and is joined and secured at joint 615. Shell 610 provides a rigid frame or structure and forms a self-reacted structure to prevent expansion of compliant body 620 beyond the periphery of the shell 610. In one example, the compliant body 620 is connected to the inner periphery of shell 610. In one example, compliant body 620 and shell 610 are tubular structures.

Shell 610 and compliant body 620 are connected in a manner to bring the inner periphery of the compliant body 620 into intimate contact with the outer periphery of artery 105.

Device 600 is secured to the vasculature with an anchor structure. In this example, since the compliant body 620 is in intimate contact with the outer periphery of artery 105, a friction force is generated by joint 615.

In operation, as the artery 105 distends during systole, the compliant body 600 is exposes to pulsatile pressure loads creating a positive differential pressure. As the compliant body 600 is bounded about the outer periphery by shell 610, a positive differential pressure deforms the compliant body 620 such that an equivalent volume of blood occupies the space of the compliant volume. Under negative differential pressure, compliant body 620 returns to the original undeformed position.

Figure 7:
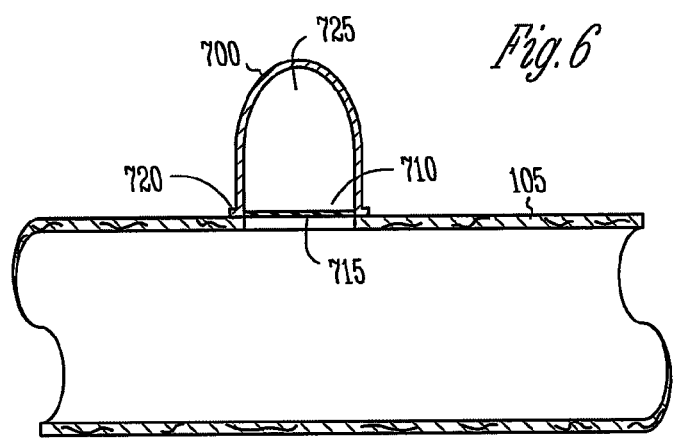
FIG. 7 illustrates a lateral cross sectional view of one embodiment of an extra-vascular compliant member according to one example.
Figure 8:
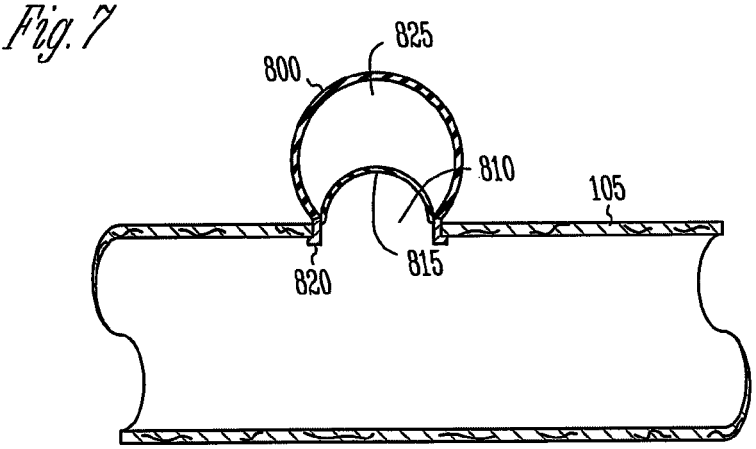
FIG. 8 illustrates a lateral cross sectional view of one embodiment of an extra-vascular compliant member according to one example.

FIGS. 7 and 8 illustrate lateral cross sectional views of examples of extra-vascular devices 700 and 800, respectively. In FIG. 7, device 700 includes compliant volume 725 defined by a flexible membrane 715 and the walls of device 700. The undeformed shape of the compliant volume can assume many shapes including, but not limited to, cylindrical, ellipsoidal, polygonal volumes with mitered, concave or convex features along the length of the compliant volume. In this example, membrane 715 has a flat, circular cross-sectional area and a length specified to encompass a volume sufficient to realize the desired therapeutic effect. In one example, membrane 715 is concave with respect to the compliant volume.

Membrane 715 is located at aperture 710 and provides a fluid-tight joint between 725 and the lumen of artery 105.

Device 700 is secured to the vasculature or surrounding tissue with feature 720 or by other anchor structure. In the example shown, feature 720 can include a suture however an adhesive or endothelial growth can also provide an anchor. In this example, feature 720 is disposed on an external surface of artery 105.

In the operation, membrane 715 is exposed to pulsatile pressure loads in artery 105. Under positive differential pressure, blood flowing in artery 105 presses against the device 700 and deforms membrane 715 such that an equivalent volume of blood occupies the space of the compliant volume. Under negative differential pressure, membrane 715 returns to the original, undeformed position.

FIG. 8 illustrates an example in which device 800 includes a wall fabricated of a resilient material. Volume 825 has a variable volume based on deflection of device 800 and position of membrane 815. Membrane 815 is located at aperture 810. Feature 820 provides an anchoring structure for affixing device 800 to artery 105. Feature 820 is disposed on an interior surface of artery 105. Device 800 assumes a generally bulbous shape with increasing pressure within artery 105.

Figure 9:
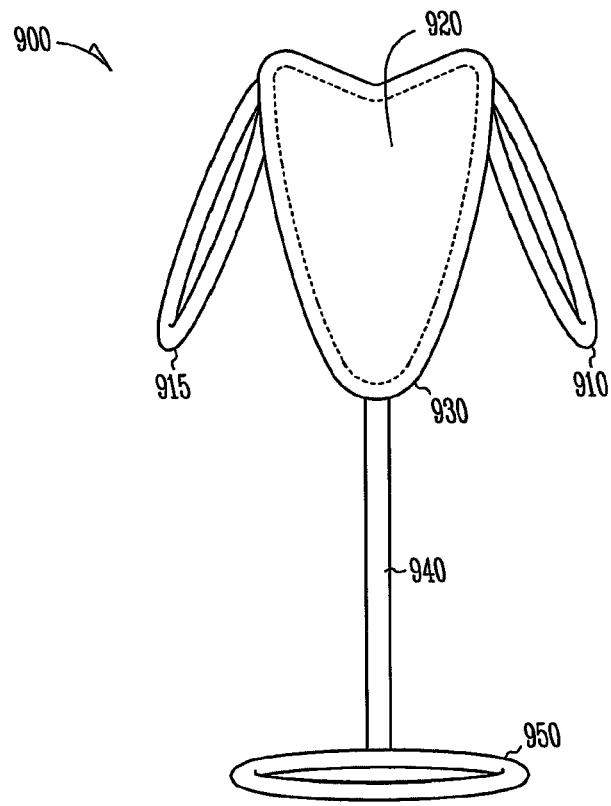
FIG. 9 illustrates an elevation view of a device according to one example.
Figure 10:
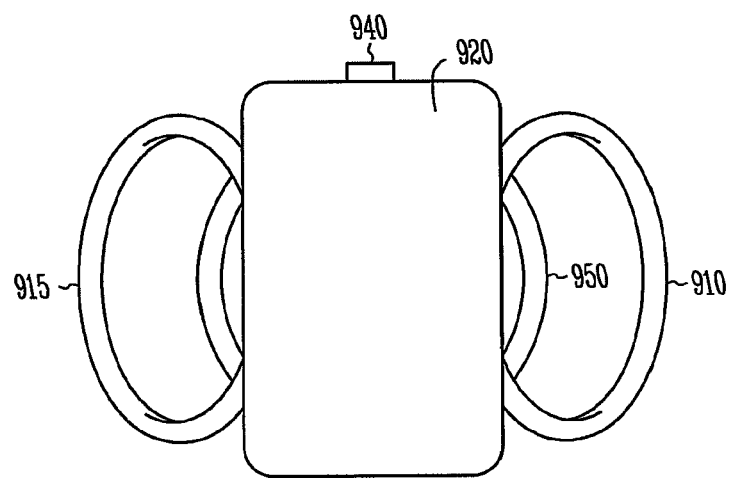
FIG. 10 illustrates a top view of a device according to one example.

FIGS. 9 and 10 illustrate device 900 having compliant body 920 and a central compliant volume. FIG. 9 illustrates a front view and FIG. 10 illustrates a top view. Device 900 is configured for placement within the branches of a main pulmonary artery (left and right). The undeformed shape of the central compliant volume is defined by a flexible membrane of body 920 that can assume many shapes including, but not limited to, cylindrical, ellipsoidal, polygonal cross-sections with mitered, concave, or convex features along the length of the central compliant volume. In this example, the flexible membrane forms a triangular volume shape of a given length, base and height based on the central compliant volume required for specific patient therapeutic requirements. In one example, one or more surfaces defined by the flexible membrane can be of a different material with different stiffness and compliance properties.

Device 900 is secured within the blood vessel lumen with an anchor structure. In this example, compliant body 920 is secured within blood vessel lumen by a scaffold-like structure for placement near a bifurcating vasculature anatomy. The scaffold-like structure includes structural rings 910 and 915 attached to the support structure base 930 at angles from 0 to 180 degrees as defined by an included angle measured from a surface of the compliant body 920 to the planar surface of structural ring 910 or 915. Structural rings 910 and 915 can be located in or near the bifurcating vasculature anatomy, respectively, to anchor the compliant body 920 at, or near, the bifurcation and are distributed around the periphery of the support structure base 930 at a location to locate structural rings 910 and 915 in the bifurcating vessels.

A diameter of rings 910 and 915 are a function of the diameter of the bifurcating vessels.

The support member 940 attaches to the support structure base 930 at appropriate locations along the periphery of the support structure base 930 at a first end and to the lower support base 950 at appropriate locations along the periphery of the lower support base 950 at the second end. The support member 940 and lower support base 950 are located in the primary vessel with support member 940 of a length to provide the support structure base 930 with sufficient lateral support to prevent embolization during systolic/diastolic heart function. The diameter of lower support base 950 is selectable based on the anatomy of the particular patient into which the device will be inserted. Support structures 910, 915, 930, 940, and 950 are made of biocompatible, shape memory alloy materials such nitinol.

In one example, device 900 is secured in position to allow the compliant body 920 to be suspended within the blood vessel lumen.

In the operation, the compliant body 920 is exposes to pulsatile pressure loads in the blood vessel lumen. Under positive differential pressure, blood flowing in the vessel lumen presses against the device 900 and deforms the flexible membrane such that an equivalent volume of blood occupies the space of the compliant volume. Under negative differential pressure, the flexible membrane returns to the original, undeformed position.

Device 900 provides increased vessel compliance and is configured to divert acoustic waves to reduce reflections and the effects of afterloading.

Figure 11:
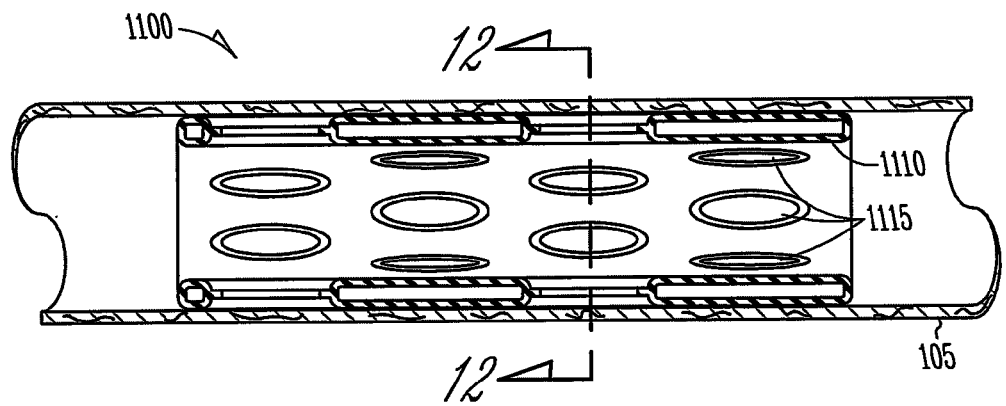
FIG. 11 illustrates a sagittal view of a fenestrated device according to one example.
Figure 12:
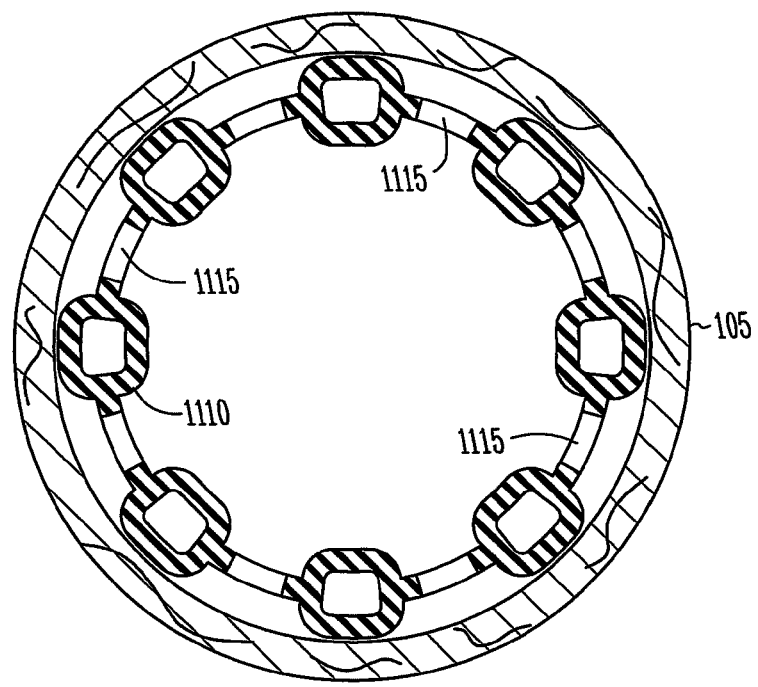
FIG. 12 illustrates a transverse view of a fenestrated device according to one example.

FIGS. 11 and 12 illustrate a sagittal and transverse cross sectional views, respectively, of fenestrated device 1100 in artery 105. Device 1100 includes compliant body 1110 in the form of a toroidal balloon. A plurality of fenestrations 1115 are provided in the balloon and the perimeter of each fenestration 1115 is bonded to retain a closed volume within compliant body 1110. The bonded perimeters of each fenestration 1115 presents an appearance similar to that of quilt stitching. The aperture of each fenestration 1115 provides a region where endothelium cells on the inner walls of artery 105 infuse and bond with the compliant body 1110, thus holding device 1100 at a fixed location within artery 105. Between adjacent fenestrations 1115, the balloon walls are separated by a distance that is maximal at the midway point between the fenestrations and tapers uniformly to the bonded joint at the perimeter of the fenestrations. Fenestrations 1115 are depicted as oval shapes and in various examples, can include longitudinal slits or rectangular windows.

When inflated with a pre-charge of gas, the portions of compliant body 1110 located between adjacent fenestrations may take on a faceted appearance in which the portions of compliant body 1110 that are bonded to the inner wall of artery 105 are joined by relatively straight segments of inflated balloon material. In FIG. 12, the cell growth between the compliant body 1110 and the wall of artery 105 is not shown. The web of material between the fenestrations can be biased to enlarge the bore of the lumen by selection of suitable materials for the inner and outer portions of the toroidal balloon, by selection of material thickness. In addition, an internal structure can be molded within the balloon to provide a specified bore. Furthermore, an installation tool having a stent-like support structure can be used to temporarily bring the web into contact with the vessel wall and thereby promote endothelial cell growth.

The number of fenestrations and the arrangement of fenestrations and balloon material can be tailored to provide a larger or smaller number of contact points with the arterial wall. In addition, adjacent balloon segments (defined between fenestrations) can be independent or continuous.

The compliant volume of device 1100 is defined by the toroidal balloon and lies between the fenestrations. The undeformed shape of device 1100 is defined by a flexible membrane of compliant body 1110 into which a quilted pattern of holes 1115 is fenestrated to allow endothelial tissue growth over the surface of the flexible membrane. The undeformed shape of the compliant volume can assume many shapes including, but not limited to, cylindrical, ellipsoidal, polygonal cross-sections with mitered, concave or convex features along the length of the compliant volume. In this example, the flexible membrane is formed into a toroidal cylindrical shape of a length and diameter based on the compliant volume required for specific patient therapeutic requirements. In one example, device 1100 is separated into individual compliant bodies 1110 of a length less than the total length required to achieve specific patient therapeutic requirements and deployed into the artery 105 to convenient locations as required to realize the compliant volume required for patient therapeutic requirements.

Device 1100 is secured to the vasculature by an anchor structure or feature. In the example shown, the diameter of the flexible membrane is selected to ensure intimate contact of the flexible membrane with the artery 105 wall resulting in sufficient friction between the flexible membrane and the artery 105 wall to prevent embolization of device 1100.

In operation, device 1100 is located within the vasculature and the compliant body 1110 is exposed to pulsatile pressure loads. Under positive differential pressure, blood flowing in the blood vessel lumen of artery 105 presses against the compliant body 1110 and deforms the flexible membrane such that an equivalent volume of blood occupies the space of the compliant volume. Under negative differential pressure, the flexible membrane returns to the original, undeformed position.

Figure 13:
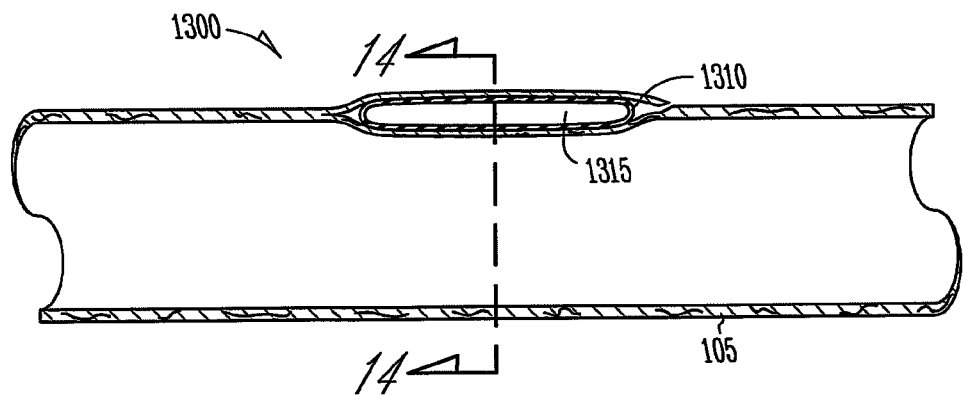
FIG. 13 illustrates a lateral view of an embedded device according to one example.
Figure 14:
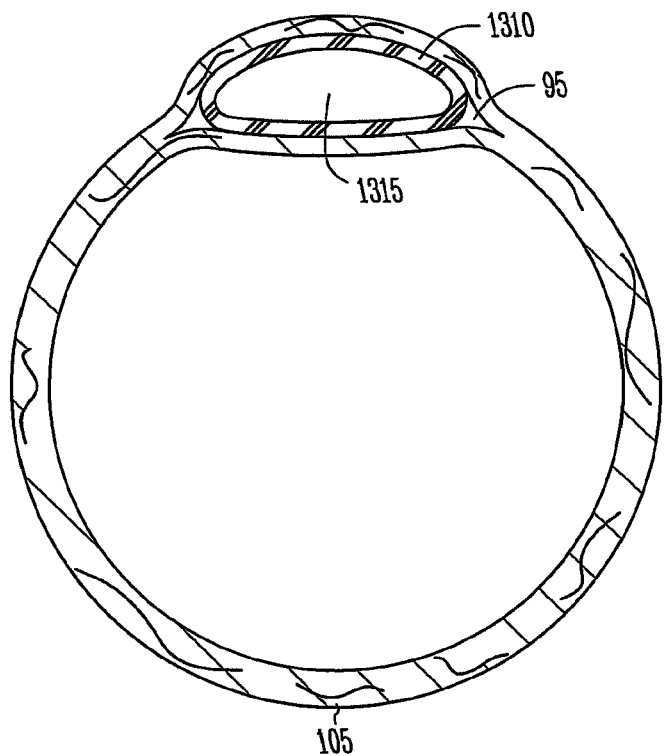
FIG. 14 illustrates a transverse view of an embedded device according to one example.

FIGS. 13 and 14 illustrate lateral and transverse cross sectional views of device 1300 according to one example. In the figures, device 1300 includes compliant body 1310 with a central compliant body 1310 with a central compliant volume 1315, the undeformed shape of which is defined by a flexible membrane designed for implantation between and within the muscular layers of a blood vessel, such as artery 105. The undeformed shape of the central compliant volume 1315 defined by a flexible membrane (in the form of a balloon) can assume many shapes including, but not limited to, cylindrical, ellipsoidal, polygonal cross-sections with mitered, concave, or convex features along the length of the central compliant volume 1315. In this embodiment, the flexible membrane is formed into an oblong cylindrical cross-sectional shape of a given length and central diameter based on the central compliant volume 1315 required for patient therapeutic requirements.

Device 1300 is secured to the vasculature with an anchor structure. In this example, device 1300 is positioned between muscular layers of artery 105 ensuring intimate contact of the device 1300 with the artery 105, thus resulting in sufficient friction between the flexible membrane and the lumen wall of artery 105 to prevent embolization of the device 1300.

In operation, device 1300 is located within the vasculature and is exposed to pulsatile pressure loads. Under positive differential pressure, blood flowing in the vessel lumen of artery 105 presses against the blood vessel lumen wall which in turn deforms the flexible membrane of compliant body 1310 such that an equivalent volume of blood occupies the space of the compliant volume 1315. Under negative differential pressure, the flexible membrane returns to the original, undeformed position as defined insertion within the artery 105.

FIG. 13 depicts device 1300 located within void 95 of an interior portion of the vessel wall. Void 95 can include a region between two layers of a wall or within a single particular layer.

Figure 15:
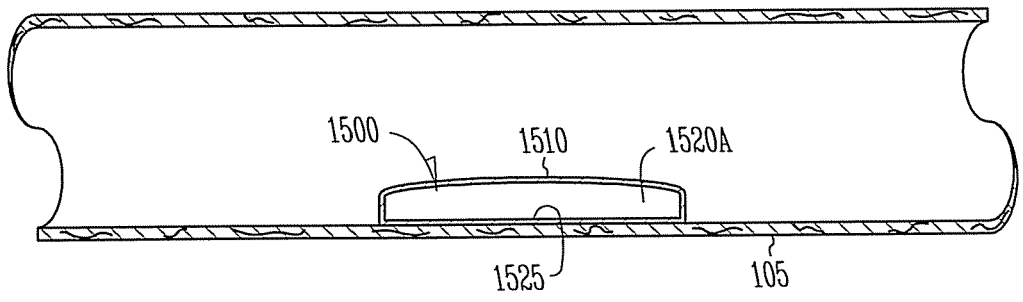
FIGS. 15 and 16 illustrate lateral views of a bi-modal device according to one example.
Figure 16:
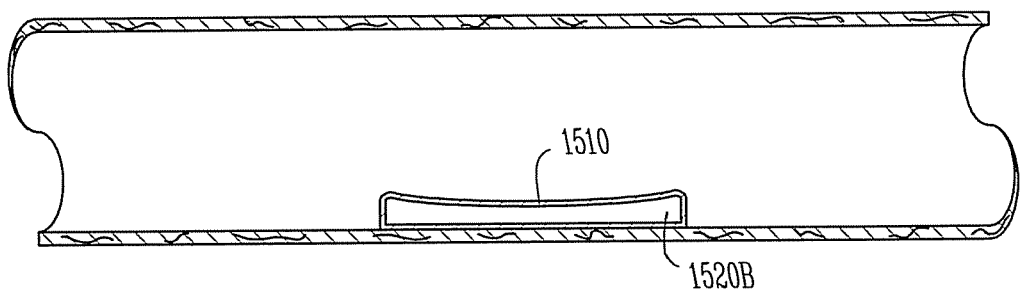

FIGS. 15 and 16 illustrate lateral cross sectional views, of device 1500 according to one example. In the example shown, device 1500 includes frame 1525 and diaphragm 1510 which cooperatively define a volume. Diaphragm 1510 is two stable modes and in one example, includes a flexible membrane. The flexible membrane can include a polymer or a metal (formed or stamped) to have bimodal configurations. In FIG. 15, diaphragm 1510 is illustrated to bow away from frame 1525 and extend into the lumen of artery 105, thereby defining volume 1520A. In FIG. 16, diaphragm 1510 is illustrated to bow toward frame 1525 and away from the center of the lumen of artery 105, thereby defining volume 1520B. Volume 1520B is less than volume 1520A and the air or gas therebetween can be vented to a larger region. In each of the two illustrated modes, diaphragm 1510 remains stable without undue influence.

Diaphragm 1510 can maintain one of two stable positions, namely, a state of negative differential pressure (FIG. 15) and a state of positive differential pressure (FIG. 16).

Device 1500 includes a compliant body with a central compliant volume (1520A and 1520B) the undeformed shape of which is defined by a diaphragm 1510 which is configured to remain in either a concave mode or a convex mode with respect to the central compliant volume. The undeformed shape of the central compliant volume defined by a diaphragm 1510 can assume many shapes including, but not limited to, cylindrical, ellipsoidal, polygonal cross-sections with mitered, concave, or convex features along the length of the central compliant volume. In the example shown, the diaphragm 1510 is formed into a rectangular cross-sectional shape of a given length based on the central compliant volume required for patient therapeutic requirements.

Device 1500 is secured to the vasculature using frame 1525. In this example, frame 1525 can be sutured to a blood vessel lumen wall (artery 105) to prevent embolization of the device 1500. In one example, Device 1500 is located within the blood vessel lumen and is held in a fixed position by other structure to suspend device 1500 within the lumen.

In operation, device 1500 is located within the blood vessel lumen and is exposed to pulsatile pressure loads. Under positive differential pressure, blood flowing in the blood vessel lumen presses against the diaphragm 1510 until such time that sufficient force is generated over the area of the diaphragm 1510 that the buckling strength of the flexible membrane is exceeded and the diaphragm 1510 becomes convex with respect to the central compliant volume. Under negative differential pressure, the pressure contained within the central compliant volume presses against the diaphragm 1510 until such time that sufficient force is generated over the area of diaphragm 1510 that the buckling strength of diaphragm 1510 is exceeded and diaphragm 1510 becomes concave with respect to the central compliant volume whereby the diaphragm 1510 is returned to the original, undeformed position.

Figure 17:
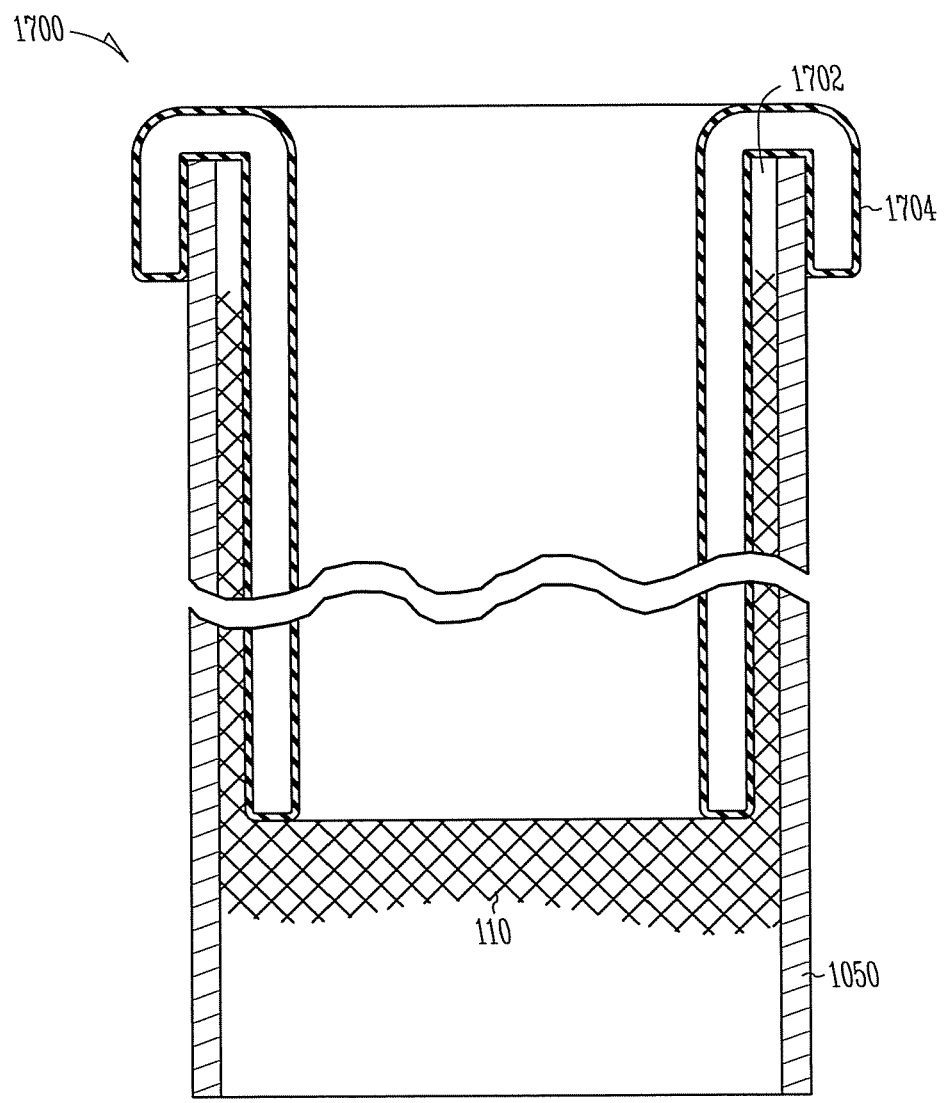
FIG. 17 illustrates a view of a device according to one example.

FIG. 17 illustrates a portion of device 1700 according to one example. Device 1700 includes coaxial outer tube 1050 and inner tube 1704 having a rolled, or everted end as shown at the top of the figure. Void 1702 between outer tube 1050 and inner tube 1704 provides a variable volume region. Inner tube 1704 is fabricated of an elastic or compliant material. Void 1702 can be precharged with a predetermined pressure. Variations in fluid pressure in a fluid (such as blood) flowing through the lumen of inner tube 1704 will cause a change in the volume at void 1702. A port in outer tube 1050 can be used to provide a precharge.

Device 1700 can be held in a fixed position within and artery or organ using interface 110 or other anchor structure.

Additional Notes

The energy storage device includes a membrane in one example. The membrane provides a barrier to separate the blood (or other fluid) from the variable volume region. The membrane, in one example, is unstressed until the onset of pressure from the fluid. With the onset of pressure, the membrane is deflected from the initial position and takes on a distended mode. Modulation of pressure within the organ causes a corresponding modulation of the membrane position. The pressure in the variable volume region will also modulate with change in position of the membrane.

In one example, the variable volume region is pressurized with a pre-charge including a gas or a fluid. The pre-charge can be delivered by a syringe, conversion of a liquid or solid substance to a gaseous phase (i.e., to off-gas a vapor), or by physical manipulation of the membrane. A variable volume region can have a pre-charge gas pressure selected based on various factors, including, for example, the blood pressure or the stiffness of the membrane. In one example, the pre-charge is approximately 85% of the typical pressure in that organ.

In one example, the variable volume region can be pressurized after implantation. As such, a syringe or other means can be used to recharge the energy storage device. Recharging can include directly injecting a gas or fluid into the device. The injection can be delivered through a port on an exterior portion of the body (or through an arterial wall).

The variable volume region can be pressurized using a compressible gas such as carbon dioxide, air, nitrogen, argon, helium, or other gas. In one example, a large molecule gas is selected to reduce incidence of gas leak-down through the membrane. In one example, nitric oxide is selected for pressurizing the region. Nitric oxide gas leaked from a membrane and into an artery can provide a therapeutic benefit to the tissue.

An example of the present subject matter can be implanted in the pulmonary artery. Other locations include placement in the right of left main pulmonary artery (MPA).

In one example, a device is located within a lumen of the artery and retained by a suspension or support structure. The device presents a volume that varies with pressure changes. In one example, the device is coupled to an artery by a fluid-tight joint. The fluid tight joint can be the result of endothelial cell development, by an adhesive, or other structure.

In one example, the energy storage device is passively operated based on pressure dynamics within the organ. As the pressure rises, energy is absorbed and upon reduction in pressure, the energy is returned to the fluidic system. In one example, the energy storage device is actively modulated. Active modulation can include a motor-driven piston or membrane, a piezo-electric element, or other device that can be modulated by an external energy source.

In one example, a plurality of compressible gaseous bubbles can be delivered to the organ using a suitable manifold. The volume of the bubbles will modulate with changes in the pressure within the fluidic system. The delivery manifold can include an annular ring configured to emit bubbles into the organ.

A variety of energy storage devices can be used in the present system. In one example, such a device includes a sealed gas chamber above a bodily fluid (such as blood). The gas chamber (or variable volume region) can be separated by a fluid-gas interface (without a barrier or membrane) or can include a resilient membrane (diaphragm). The membrane can be in the form of a planar diaphragm or in the form of a bladder or balloon. The membrane can take a continuously variable position within its range of freedom or can have any number of indexed modes. For example, a bi-stable membrane can have a first mode or a second mode corresponding to different volumes.

In one example, the energy storage device includes a gas-charged piston or a spring-loaded piston. A gas-charged piston example includes a free-floating piston with a seal between the piston wall and the cylinder wall.

The energy storage device can be located internal to an organ (e.g., wholly within the channel), external to the organ (e.g., coupled to an artery by a fluidic channel), or located partially internal and partially external (e.g., in a wall of a vessel).

The surface area of the membrane, working deflection range of the membrane, and the pre-charge of the variable volume region can be selected to suit a particular application. In addition, multiple devices can be used in series or in parallel configuration.

What is claimed is:

1. A device configured to be implanted in a pulmonary artery to treat pulmonary hypertension, the device comprising:
    a balloon having an outer surface and a cylindrical shape, the balloon sized and shaped to be fully implanted within the pulmonary artery and configured to receive a compressible fluid;
    an interface sized and shaped to be fully implanted within the pulmonary artery and configured to expand upon deployment to intimately contact a wall of the pulmonary artery, the interface configured to be coupled to the balloon so that the balloon is suspended within a lumen of the pulmonary artery such that the balloon compresses under positive differential pressure where blood is permitted to flow between the outer surface of the balloon and an inner surface of the wall of the pulmonary artery, the balloon further configured to return to an original, expanded position under negative differential pressure where blood is permitted to flow between the outer surface of the balloon and the inner surface of the wall of the pulmonary artery, the interface having an external surface configured to bond with the wall of the pulmonary artery; and
    a coating disposed on the balloon to limit diffusion of the compressible fluid through the balloon.

2. The device of claim 1, wherein the interface is aligned with a longitudinal axis of the balloon.

3. The device of claim 1, wherein the interface includes at least one of a scaffold or stent.

4. The device of claim 1, wherein the external surface is configured to enable endothelial cell development.

5. The device of claim 1, wherein the interface is configured to provide a fluid-tight joint with the wall of the pulmonary artery.

6. The device of claim 1, wherein the interface comprises a metal mesh.

7. The device of claim 1, wherein the interface comprises a non-metal mesh.

8. The device of claim 1, wherein the balloon is configured to deform such that an equivalent volume of blood occupies a space in the pulmonary artery adjacent the balloon.

9. A balloon configured for inflation using a compressible gas in a pulmonary artery to treat pulmonary hypertension, the balloon comprising an outer surface configured for affixation within a wall of the pulmonary artery and a coating configured to limit diffusion of the compressible gas through the balloon; and
    an interface configured to be coupled to the balloon and to expand upon deployment to intimately contact the wall of the pulmonary artery,
    wherein the balloon is configured to be fully implanted within the pulmonary artery and to compress under positive differential pressure where blood is permitted to flow between the outer surface of the balloon and the wall of the pulmonary artery, the balloon further configured to return to an original, expanded position under negative differential pressure where blood is permitted to flow between the outer surface of the balloon and the wall of the pulmonary artery.

* * * * *